United States Patent
Ha et al.

(10) Patent No.: US 10,716,948 B2
(45) Date of Patent: Jul. 21, 2020

(54) RADIO FREQUENCY POWERED ADIABATIC STIMULATION WITH ENERGY REPLENISHMENT

(71) Applicant: The Regents Of The University Of California, Oakland, CA (US)

(72) Inventors: Sohmyung Ha, La Jolla, CA (US); Gert Cauwenberghs, San Diego, CA (US); Chul Kim, La Jolla, CA (US); Jiwoong Park, La Jolla, CA (US); Patrick P. Mercier, San Diego, CA (US); Abraham Akinin, La Jolla, CA (US); Hui Wang, La Jolla, CA (US); Christoph Hans Maier, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 141 days.

(21) Appl. No.: 15/736,252

(22) PCT Filed: Jun. 15, 2016

(86) PCT No.: PCT/US2016/037670
§ 371 (c)(1),
(2) Date: Dec. 13, 2017

(87) PCT Pub. No.: WO2016/205398
PCT Pub. Date: Dec. 22, 2016

(65) Prior Publication Data
US 2018/0169422 A1  Jun. 21, 2018

Related U.S. Application Data

(60) Provisional application No. 62/175,939, filed on Jun. 15, 2015.

(51) Int. Cl.
*A61N 1/378* (2006.01)
*A61N 1/36* (2006.01)
(Continued)

(52) U.S. Cl.
CPC ......... *A61N 1/3787* (2013.01); *A61N 1/3606* (2013.01); *A61N 1/36125* (2013.01);
(Continued)

(58) Field of Classification Search
CPC ............ A61N 1/37211; A61N 1/37205; A61N 1/3787; A61N 1/3606; A61N 1/36125; A61N 1/375
(Continued)

(56) References Cited

U.S. PATENT DOCUMENTS 5,758,651 A * 6/1998 Nygard ................ A61B 5/0031
600/554
6,895,278 B1 * 5/2005 Gordon .............. A61N 1/36007
607/40

(Continued)

OTHER PUBLICATIONS

Arfin, Scott K., and Rahul Sarpeshkar. "An energy-efficient, adiabatic electrode stimulator with inductive energy recycling and feedback current regulation." IEEE transactions on biomedical circuits and systems 6.1 (2012): 1-14.
(Continued)

*Primary Examiner* — Amanda K Hulbert
*Assistant Examiner* — Philip C Edwards
(74) *Attorney, Agent, or Firm* — Mintz Levin Cohn Ferris Glovsky and Popeo, P.C.

(57) ABSTRACT

In one respect, there is provided an apparatus for neural stimulation. The apparatus may include an antenna, a plurality of electrodes, and a voltage supply generator. The antenna may be configured to receive, from an external source, radio frequency energy. The voltage supply generator configured to generate a voltage supply by at least ramping up a voltage of the radio frequency energy in successive increments, wherein the voltage supply drives a
(Continued)

current to the plurality of electrodes during neural stimulation. Related methods and computer program products are also disclosed.

18 Claims, 9 Drawing Sheets

(51) Int. Cl.
  *A61N 1/372* (2006.01)
  *A61N 1/375* (2006.01)
(52) U.S. Cl.
  CPC .......... *A61N 1/375* (2013.01); *A61N 1/37205* (2013.01); *A61N 1/37211* (2013.01)
(58) Field of Classification Search
  USPC .......................................................... 607/61
  See application file for complete search history.

(56) References Cited

U.S. PATENT DOCUMENTS

2007/0244410 A1    10/2007  Fridman et al.
2014/0058480 A1*    2/2014  Perryman .......... A61N 1/36125
                                                         607/60

OTHER PUBLICATIONS

Franks, Wendy, et al. "Impedance characterization and modeling of electrodes for biomedical applications." IEEE Transactions on Biomedical Engineering 52.7 (2005): 1295-1302.

Kelly, Shawn K., and John L. Wyatt. "A power-efficient neural tissue stimulator with energy recovery." IEEE Transactions on Biomedical Circuits and Systems 5.1 (2011): 20-29.

Lee, Hyung-Min, et al. "A power-efficient switched-capacitor stimulating system for electrical/optical deep brain stimulation." IEEE Journal of Solid-State Circuits 50.1 (2015): 360-374.

Muller, Rikky, et al. "A minimally invasive 64-channel wireless ?ECoG implant." IEEE Journal of Solid-State Circuits 50.1 (2015): 344-359.

Yeager, D., et al. "A 4.78 mm 2 fully-integrated neuromodulation SoC combining 64 acquisition channels with digital compression and simultaneous dual stimulation." VLSI Circuits Digest of Technical Papers, 2014 Symposium on. IEEE, 2014.

çilingiroglu, Ugur, and Sercan Ipek. "A zero-voltage switching technique for minimizing the current-source power of implanted stimulators." IEEE transactions on biomedical circuits and systems 7.4 (2013): 469-479.

* cited by examiner

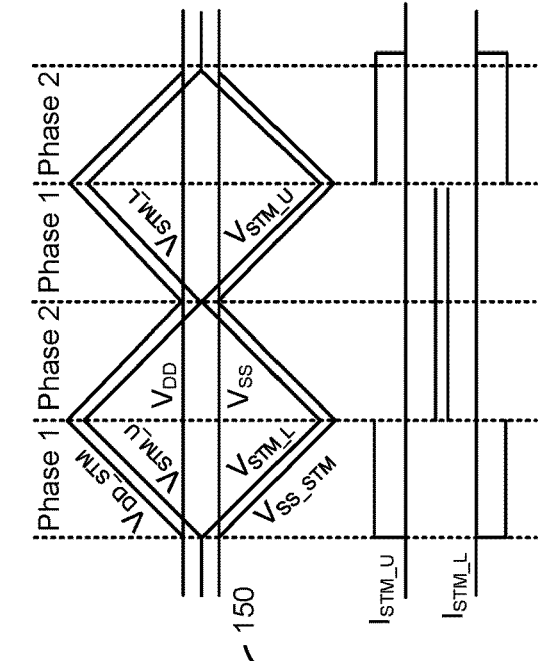
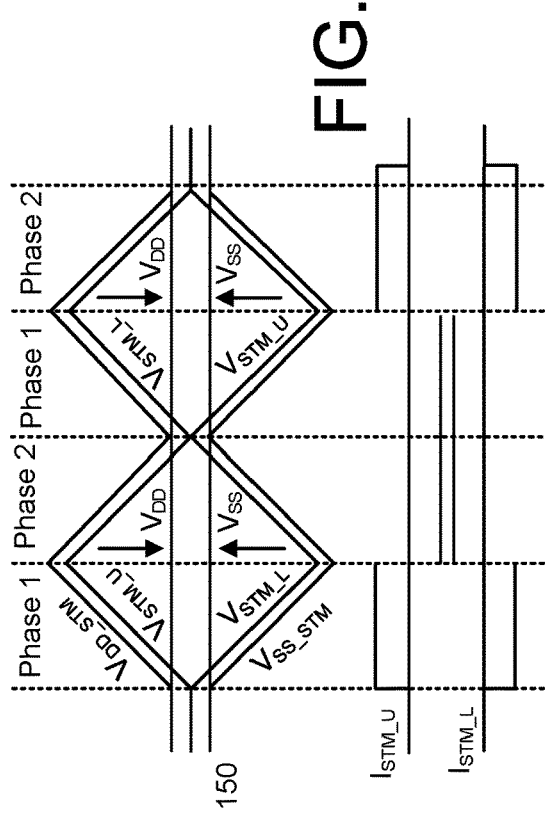
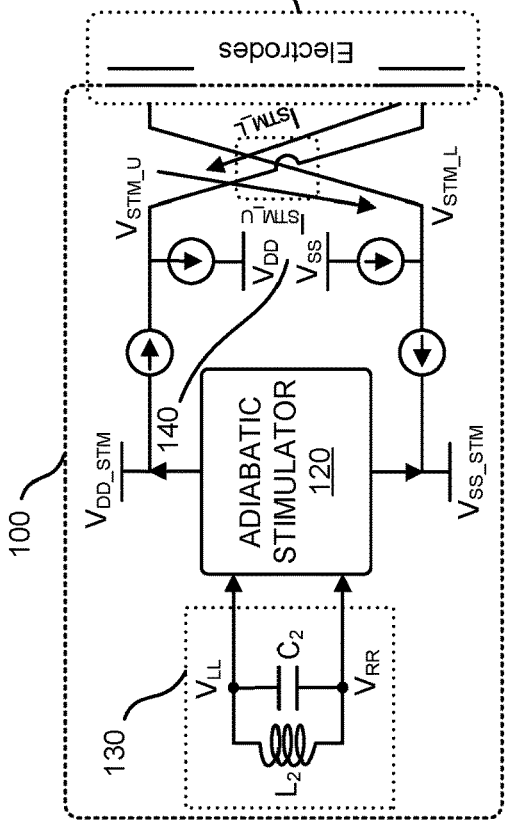
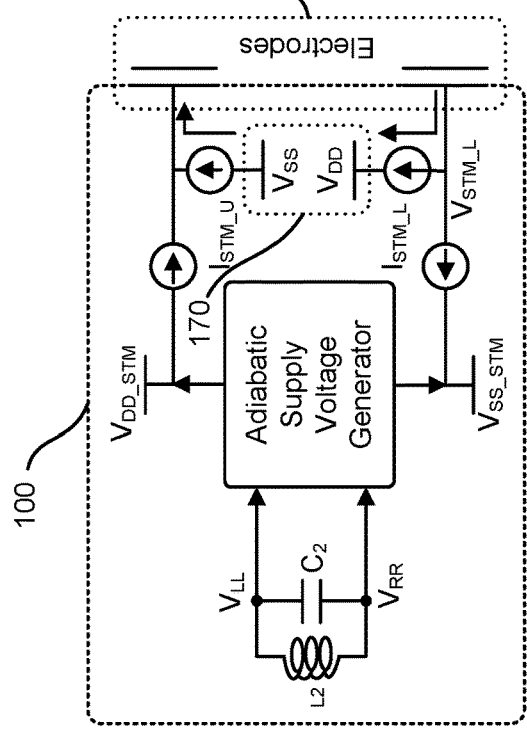
FIG. 5C
FIG. 5D

RADIO FREQUENCY POWERED ADIABATIC STIMULATION WITH ENERGY REPLENISHMENT

CROSS REFERENCE TO RELATED APPLICATIONS

This application is a national-phase entry of Patent Cooperation Treaty Application No. PCT/US2016/037670 filed Jun. 15, 2016, entitled "RADIO FREQUENCY POWERED ADIABATIC STIMULATION WITH ENERGY REPLENISHMENT," which claims the benefit of priority to U.S. Provisional Patent Application No. 62/175,939 filed Jun. 15, 2015, entitled "RF-POWERED ADIABATIC STIMULATION WITH ENERGY REPLENISHMENT," the contents of which are hereby incorporated by reference in their entirety.

TECHNICAL FIELD

The subject matter disclosed herein relates to neural stimulation and more specifically to a neural interfacing stimulation device.

BACKGROUND

Stimulation of neural tissue may be an effective treatment for a variety of physiological and psychological conditions. For instance, neural stimulation may be used in cochlear implants to provide functional hearing for deaf patients as well as in visual prosthetics (e.g., retinal implants) to restore vision. Pacemakers may also rely on neural stimulation to control and prevent incidents of, for example, cardiac rhythm irregularities (e.g., tachycardia), heart failure, and stroke. The technology may further be employed for brain stimulation to treat, for example, epilepsy, Parkinson's disease, and a variety of affective disorders (e.g., depression, obsessive compulsive disorder, chronic pain).

Conventional neural stimulators require wired connections between the electrodes and a separate power source. The bulk and weight of a typical power source (e.g., battery) prevents the power source from being implanted along with the neural stimulator. But keeping the power source external may tether a patient to the power source during treatment. This restriction in patient mobility may prevent treatment from being administered to the patient over an extended period of time. Treatment also may not be available to the patient as and when needed. Thus, conventional neural stimulators may be unable to effectively treat conditions with chronic and/or unpredictable symptoms (e.g., sudden onset of epileptic seizure). Moreover, the delivery treatments via a conventional wired neural stimulator may require invasive procedures (e.g., incisions to accommodate the wired connections), which may elevate a patient's risk of infection.

SUMMARY

Methods and articles of manufacture, including apparatuses and computer program products, are provided for neural stimulation. In some example embodiments, there is provided an apparatus that includes an antenna, a plurality of electrodes, and a voltage supply generator. The antenna may be configured to receive, from an external source, radio frequency energy. The voltage supply generator configured to generate a voltage supply by at least ramping up a voltage of the radio frequency energy in successive increments, wherein the voltage supply drives a current to the plurality of electrodes during neural stimulation.

In some variations, one or more of the features disclosed herein including the following features can optionally be included in any feasible combination. The apparatus may further include a current controller configured to at least route the current to the plurality of electrodes during an energy provision phase of neural stimulation, and route the current from the plurality of electrodes to a power source during an energy replenishment phase of neural stimulation. The current controller may be further configured to create a short circuit between the plurality of electrodes during a termination phase of neural stimulation, and wherein creating the short circuit may release energy that is not returned to the power source during a previous energy replenishment phase of neural stimulation. The power source may be configured to provide energy for one or more of a control, a configuration, a voltage bias generation, a communication, and a recording by the apparatus.

In some variations, the apparatus may further include a control unit configured to at least cause the current controller to change the routing of the current between a successive energy provision phase and energy replenishment phase of neural stimulation. The control unit may be further configured to at least select a first subset of electrodes and a second subset of electrodes from the plurality of electrodes, and designate the first subset of electrodes to serve as cathodic electrodes and the second subset of electrodes to serve as anodic electrodes. The apparatus may further include a switch matrix configured direct, based at least in part on the selection and designation by the control unit, the current to flow from the cathodic electrodes to the anodic electrodes. A third subset of electrodes may not selected, and wherein the third subset of electrodes may remain inactive during neural stimulation. The selection may be based at least in part on a location of the neural stimulation.

In some variations, the apparatus may further include a communication unit configured to receive, from the external source, one or more instructions for configuring a stimulation waveform and/or a stimulation location. The plurality of electrodes may comprise capacitive electrodes and/or pseudo capacitive electrodes. The voltage supply generator may comprise a first voltage multiplier and a second voltage multiplier, wherein the first voltage multiplier may be configured to generate a first voltage that comprises a first increment to the voltage of the radio frequency energy, and wherein the second voltage multiplier may be configured to generate a second voltage that comprises a second increment to the voltage of the radio frequency energy. The second voltage multiplier may generate the second voltage when the first voltage multiplier reaches a maximum voltage. The first voltage multiplier and/or the second voltage multiplier may comprise a charge pump.

DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 5C depicts an operation of a neural stimulator during a second energy provision phase, in accordance with some example embodiments.

FIG. 5D depicts an operation of a neural stimulator during a second energy replenishment phase, in accordance with some example embodiments.

DETAILED DESCRIPTION

Figure 1:
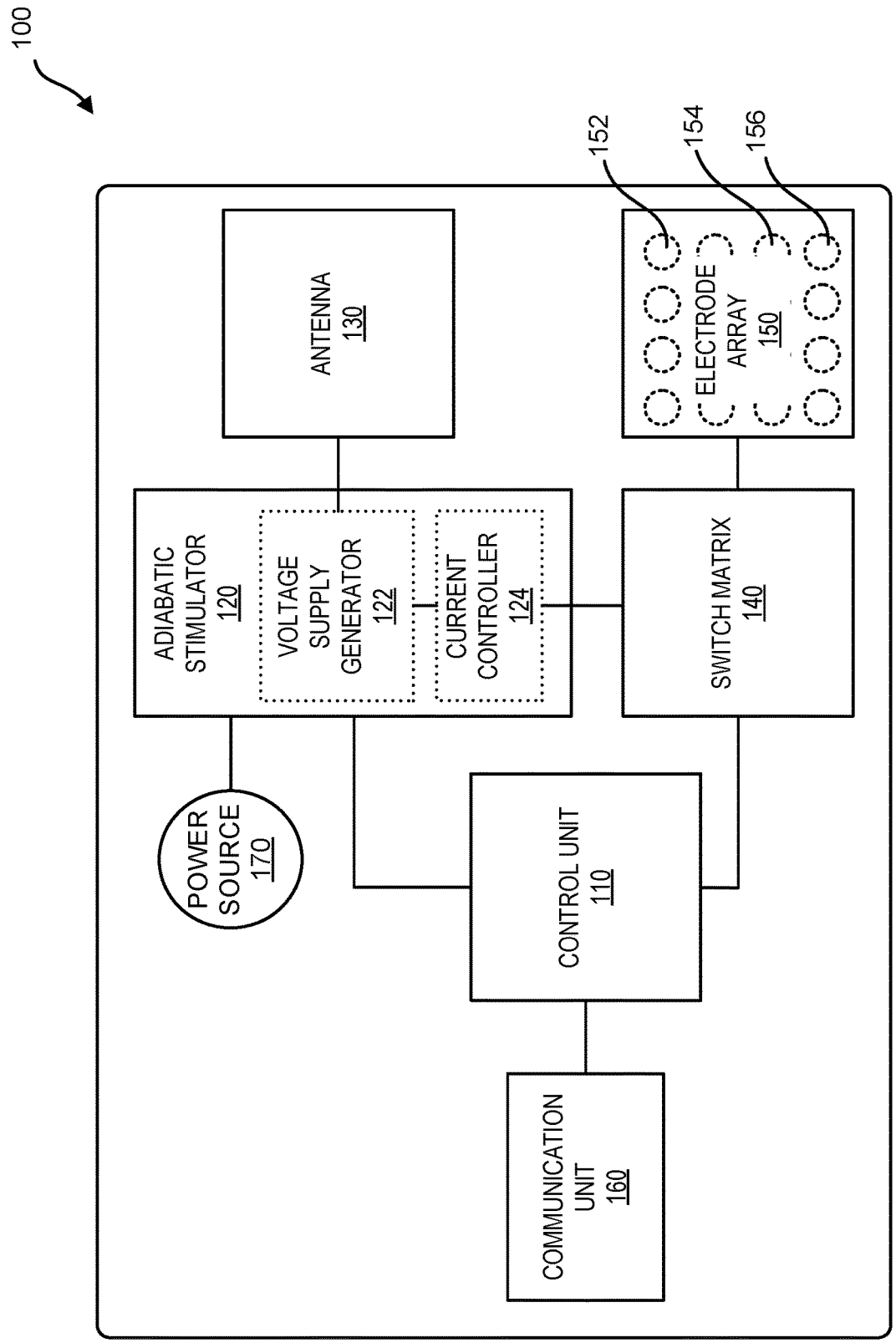
FIG. 1 depicts a block diagram illustrating a neural stimulator, in accordance with some example embodiments.

A neural stimulator may be powered wirelessly by radio frequency energy from an external source (e.g., radio frequency transceiver). The neural stimulator may include a plurality of electrodes configured to provide neural stimulation by delivering current to a treatment site (e.g., nerve tissue). The neural stimulator may further include circuitry configured to harness the radio frequency energy and generate a voltage supply that powers the electrodes. But the voltage associated with radio frequency energy may be too low to drive sufficient current through the electrodes for purposes of neural stimulation. For instance, an 8 to 9 volt voltage supply may be needed to provide the 10 nano-coulombs of charge required for typical neural stimulation treatments. But radio frequency energy may only provide a 0.8 volt voltage supply capable of delivering a mere 1.2 nano-coulombs of charge to the electrodes.

In some example embodiments, there may be provided a radio frequency powered neural stimulator that is configured to generate an adequate voltage supply from radio frequency energy. For instance, the radio frequency powered neural stimulator may include an antenna (e.g., a resonant or tank circuit) adapted to capture radio frequency energy. As such, the antenna may act as a low voltage current source. The radio frequency powered neural stimulator may further include a voltage supply generator configured to generate, from the radio frequency energy, a voltage supply capable of delivering a sufficient amount of charge (e.g., 10 nano-coulombs) for neural stimulation.

According to some example embodiments, the voltage supply generator may be configured to ramp up the voltage of the radio frequency energy (e.g., from the antenna) in successive increments. For instance, the voltage supply generator may include a plurality of voltage multipliers (e.g., charge pump circuits), which are activated sequentially to ramp up the voltage of radio frequency energy (e.g., from the antenna) to a level required for neural stimulation. This adiabatic voltage ramping process may be more energy efficient than powering the neural stimulator via a static high voltage supply. For instance, drawing a current from a high voltage supply may cause a precipitous voltage drop across the voltage supply and an excessive amount of energy loss to be lost through dissipated heat. By contrast, ramping up the voltage gradually (e.g., in increments) may avoid the precipitous voltage drop and excessive energy loss while still delivering an adequate amount of charge to the electrodes in the neural stimulator.

In some example embodiments, the radio frequency powered neural stimulator may be configured to recycle at least a portion of the charge delivered to the electrodes in the neural stimulator. For instance, charge that has accumulated at the electrodes (e.g., during administration of neural stimulation) may be returned to a separate power source that powers one or more other operations of the neural stimulator including, for example, control, configuration, voltage bias generation, communication, and recording (e.g., of intracranial electroencephalography).

FIG. 1 depicts a block diagram illustrating a neural stimulator 100, in accordance with some example embodiments. Referring to FIG. 1, the neural stimulator 100 may include a control unit 110, an adiabatic stimulator 120, an antenna 130, a switch matrix 140, an electrode array 150, a communication unit 160, and a power source 170. According to some example embodiments, the neural stimulator 100 may be implemented on a single chip (e.g., complementary metal-oxide semiconductor (CMOS)).

In some example embodiments, the antenna 130 may be adapted to capture radio frequency energy. For example, the antenna 130 can include circuitry configured to receive radio frequency signals including, for example, a resonant or tank circuit having an inductor and a capacitor connected in parallel. The radio frequency energy may trigger a flow of current through the antenna 130. As such, the antenna 130 may act as a low voltage current source. According to some example embodiments, the antenna 130 may be adapted to capture radio frequency energy having a frequency of approximately 190 megahertz.

The adiabatic stimulator 120 may be configured to provide a voltage supply for one or more electrodes in the electrode array 150. For instance, the adiabatic stimulator 120 may generate the voltage supply that drives a current through one or more electrodes in the electrode array 150. The adiabatic stimulator 120 may be further configured to recycle the energy used for neural stimulation by returning the charge accumulated at the one or more electrodes (e.g., of the electrode array 150) to the power source 170. The recycled energy stored at the power source 170 may be used to power one or more other operations of the neural stimulator 100 including, for example, control, configuration, voltage bias generation, communication, and recording (e.g., of intracranial electroencephalography).

The adiabatic stimulator 120 may be coupled with the antenna 130. For instance, the antenna 130 may provide the input rails to the adiabatic stimulator 120. As such, the adiabatic stimulator 120 may receive energy from the antenna 130. For example, radio frequency energy captured by the antenna 130 may be transferred to the adiabatic stimulator 120. The adiabatic stimulator 120 may include a voltage supply generator 122 configured to generate a voltage supply that delivers charge to one or more electrodes (e.g., in the electrode array 150). According to some example embodiments, the voltage supply generator 122 generates the voltage supply at least by ramping up the voltage of the radio frequency energy (e.g., the input rails from the antenna 130) in increments to a sufficiently high level for neural stimulation (e.g., 8 to 9 volts).

In some example embodiments, the adiabatic stimulator 120 may include a current controller 140 configured to regulate the flow of current between the adiabatic stimulator 120, the electrode array 150, and the power source 170. The adiabatic stimulator 120 may be configured to operate in phases including, for example, an energy provision phase, an energy replenishment phase, and a termination phase. According to some example embodiments, the current controller 140 may be configured to direct current from the adiabatic stimulator 120 (e.g., the voltage supply generator 122) to one or more electrodes in the electrode array 150 during the energy provision phase when energy is delivered to the one or more electrodes in order to administer electrical stimulation to a treatment site (e.g., nerve tissue). The current controller 140 may be further configured to direct current away from the electrodes (e.g., in the electrode array 150) and to the power source 170 during the energy replenishment phase. That is, during the energy replenishment phase, the current controller 140 may be configured to recycle the energy that has accumulated at the electrodes (e.g., in the electrode array 150) during a previous energy provision phase by at least storing the energy to the power source 170 for one or more subsequent and/or different uses (e.g., control, configuration, voltage bias generation, communication, and recording). During the termination phase, the current controller 140 may be configured to release any residual charge that is not recycled (e.g., returned to the power source 170) in a previous energy replenishment phase including by creating a short circuit across the electrodes.

The switch matrix 140 may be configured to direct the flow of current from the adiabatic stimulator 120 to one or more electrodes in the electrode array 150. At least a portion of the electrodes in the electrode array 150 may be selected to administer electrical stimulation by delivering current to a particular treatment site (e.g., nerve tissues). As such, the switch matrix 140 may include a plurality of switches adapted to route the flow of current from the adiabatic stimulator 120 to the electrodes (e.g., in the electrode array 150) that are selected to administer the electric stimulation. For instance, the switch matrix 140 may control (e.g., change) a direction of the current flowing through one or more electrodes in the electrode array 150.

The electrode array 150 may include a plurality of electrodes (e.g., sixteen). For instance, the electrode array 150 may include a plurality of capacitive electrodes and/or pseudo capacitive (e.g., platinum) electrodes. One or more electrodes included in the electrode array 150 may be activated (or deactivated) individually. Moreover, a first subset of active electrodes in the electrode array 150 (e.g., a first electrode 152) may be designated to serve as the cathodic electrodes while a second subset of active electrodes in the electrode array 150 (e.g., a second electrode 154) may be designated to serve as the anodic electrodes. As such, during neural stimulation, current from the adiabatic stimulator 120 may be routed (e.g., by the switch matrix 140) between the first subset of anodic electrodes and the second subset of cathodic electrodes. For instance, current (e.g., from the adiabatic stimulator 120) may be directed to flow from the first electrode 152 to the second electrode 154. Meanwhile, non-activated electrodes in the electrode array 150 (e.g., a third electrode 156) may remain inactive during neural stimulation.

In some example embodiments, the communication unit 160 may be configured to receive, from an external source, one or more configurations for the neutral stimulator 100. For example, the communication unit 160 may receive treatment parameters including, for example, stimulation waveform (e.g., arbitrary waveform, rectangular waveform) and stimulation location (e.g., selection of electrodes to be activated for stimulation).

The control unit 110 may be configured to control an overall operation of the neural stimulator 100 including by controlling the functions of the adiabatic stimulator 120 and the switch matrix 140. For instance, the control unit 110 may be, for example, a microcontroller and/or a microprocessor (e.g., general purpose processor). The control unit 110 may control the overall operation of the neural stimulator 100 based on preconfigured instructions and/or configurations received by the communication unit 160 (e.g., from an external source). For example, the control unit 110 may control when the adiabatic stimulator 120 transitions between different operational phases (e.g., energy provision, energy replenishment, and termination) by at least controlling how the current controller 124 routes current flow. The control unit 110 may further control the electrodes that are activated for the administration of neural stimulation including by controlling the current routing performed by the switch matrix 140.

Figure 2:
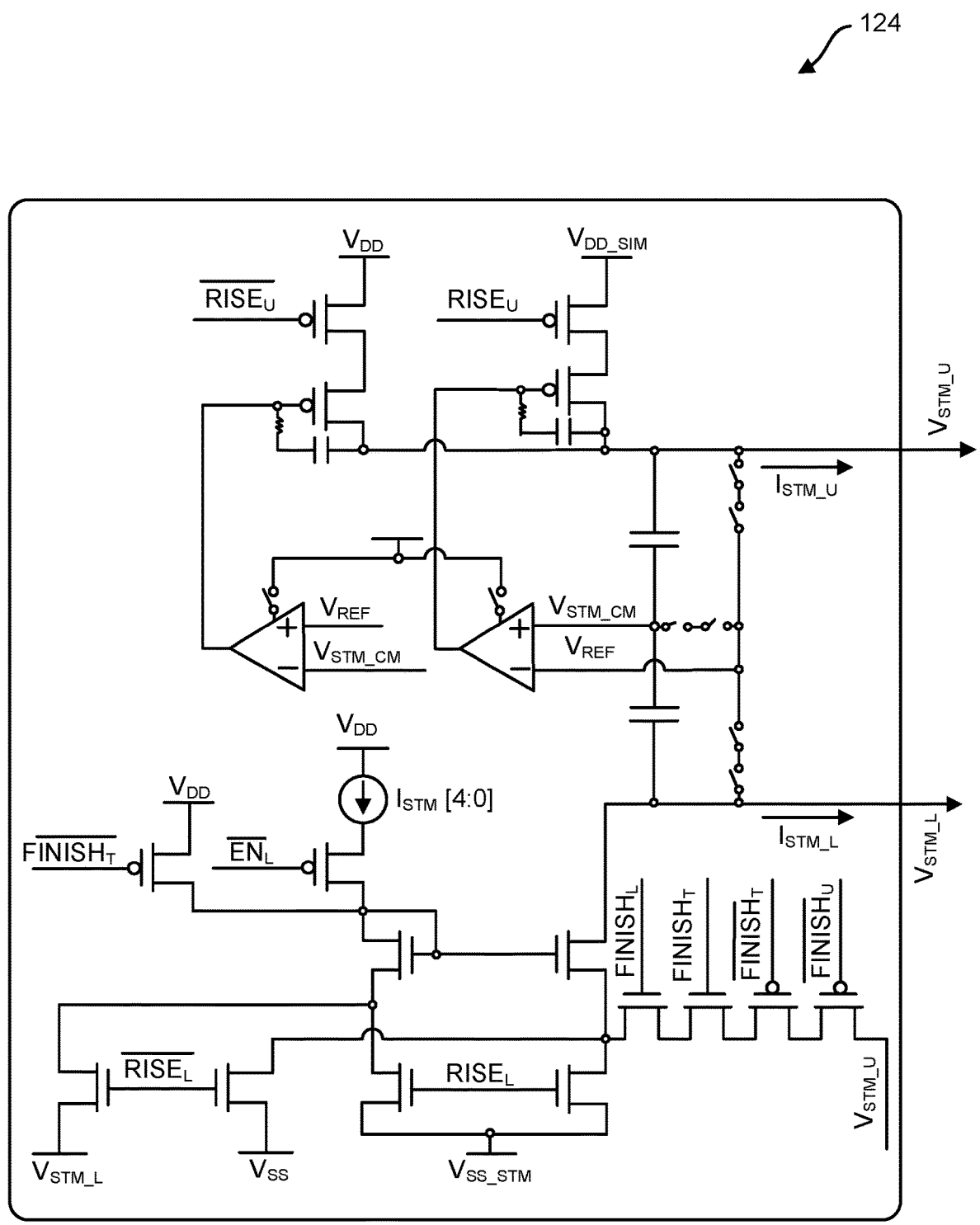
FIG. 2 depicts a schematic diagram illustrating a current controller, in accordance with some example embodiments.

FIG. 2 depicts a schematic diagram illustrating the current controller 124, in accordance with some example embodiments. Referring to FIGS. 1-2, the current controller 124 may be configured to direct the flow of current between the adiabatic stimulator 120 (e.g., the voltage supply generator 122), the electrode array 150 (e.g., via the switch matrix 140), and the power source 170. As shown in FIG. 2, the current controller 124 may be connected to the output rails (e.g., $V_{DD\_STM}$ and $V_{SS\_STM}$) of the voltage supply generator 122. The current controller 124 may also be connected to the input rails (e.g., $V_{STM\_U}$ and $V_{STM\_L}$) of the electrode array 150. The current controller 124 may be further connected to the input rails (e.g., $V_{DD}$ and $V_{SS}$) of the power source 170.

Figure 3:
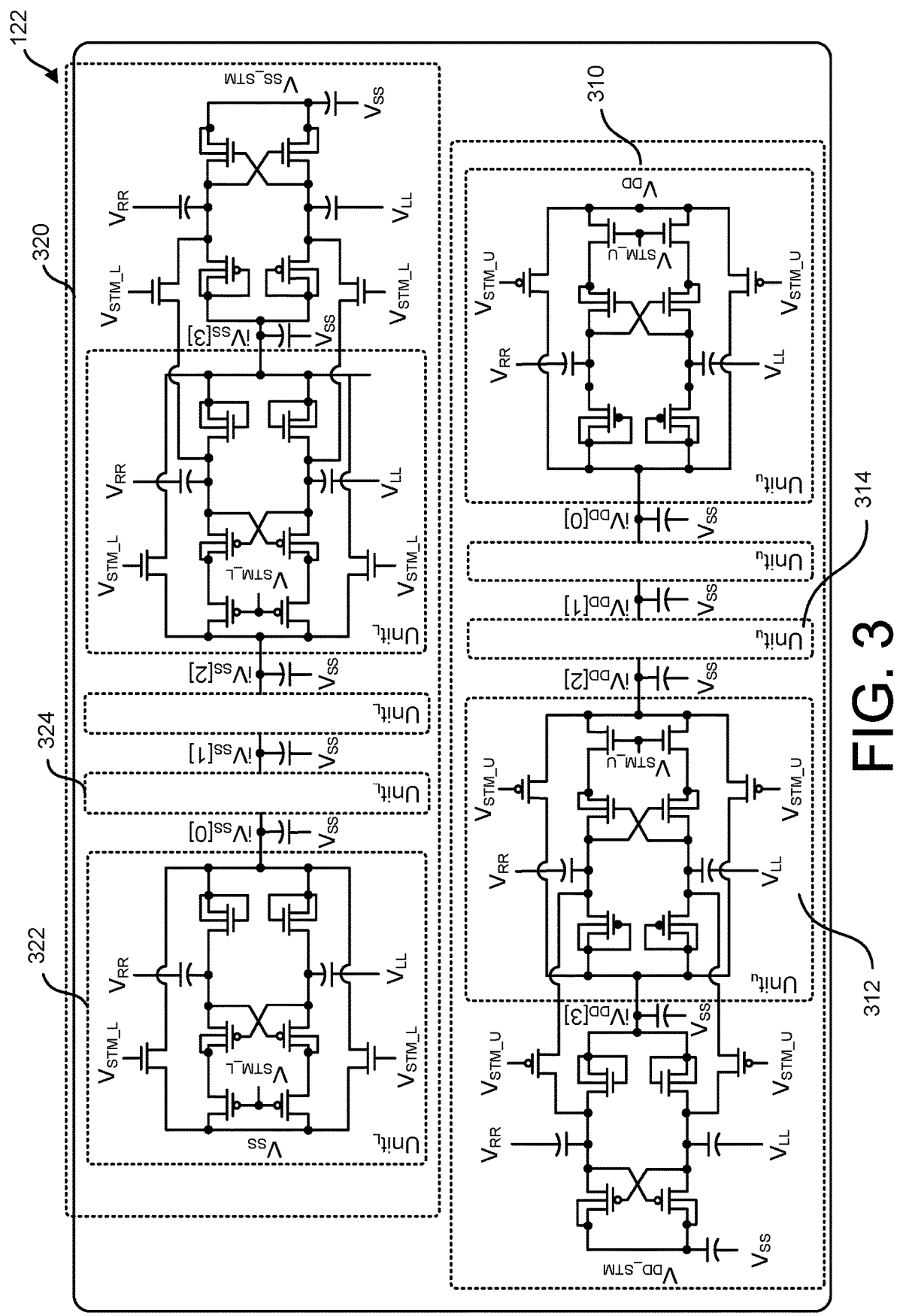
FIG. 3 depicts a schematic diagram illustrating a voltage supply generator, in accordance with some example embodiments.

FIG. 3 depicts a schematic diagram illustrating the voltage supply generator 122, in accordance with some example embodiments. Referring to FIGS. 1 and 3, the voltage supply generator 122 may be configured to provide a positive voltage supply $V_{DD\_STM}$ and a negative voltage supply $V_{SS\_STM}$. As such, the voltage supply generator 122 may include a first current path 310 for generating the positive voltage supply $V_{DD\_STM}$ and a second current path 320 for generating the negative voltage supply $V_{SS\_STM}$. As shown in FIG. 3, each current path may include a plurality of charge multipliers (e.g., charge pumps). For example, the first current path 310 may include a first charge pump 312 and a second charge pump 314 for generating the positive voltage supply $V_{DD\_STM}$. The second current path 320 may include a third charge pump 322 and a fourth charge pump 324 for generating the negative voltage supply $V_{SS\_STM}$. The voltage supply generator 122 may include a different number and/or type of charge multiplier than shown without departing from the scope of the present disclosure.

In some example embodiments, the voltage supply generator 122 may be configured to incrementally ramp up the input voltages $V_{LL}$ and $V_{RR}$ (e.g., of radio frequency energy from the antenna 130) to generate the voltage supplies $V_{DD\_STM}$ and $V_{SS\_STM}$. The voltage supply generator 122 may incrementally ramp up the input voltages $V_{LL}$ and $V_{RR}$ through a stack of charge multipliers along each of the first current path 310 and the second current path 320.

For instance, the first charge pump 312 and the second charge pump 314 may form a stack of charge multipliers along the first current path 310. The input voltages $V_{LL}$ and $V_{RR}$ may be ramped up in increments to generate the positive voltage supply $V_{DD\_STM}$ as the first charge pump 312 and the second charge pump 314 are activated in succession (e.g., one after another). As shown in FIG. 3, the first charge pump 312 is expanded to indicate that the first charge pump 312 activated while the second charge pump 314 is not expanded to indicate that the second charge pump 314 has not been activated. Similarly, the input voltages $V_{LL}$ and $V_{RR}$ may be ramped up in increments to generate the negative voltage supply $V_{SS\_STM}$ as the third charge pump 322 and the fourth charge pump 324 are activated in sequence. As shown in FIG. 3, the third charge pump 322 has been activated while the fourth charge pump 324 has not been activated.

Referring again to FIG. 3, the activation of the charge pumps (e.g., the first charge pump 312, the second charge pump 314, the third charge pump 322, and the fourth charge pump 324) included in the voltage supply generator 122 may be regulated based on the voltages $V_{STM\_L}$ and $V_{STM\_U}$ of one or more electrodes at the electrode array 150. For instance, the first charge pump 312 may be activated when the voltage $V_{STM\_U}$ at the electrodes reaches the same level as an internal voltage $V_{DD}$ of the first charge pump 312. Once the first charge pump 312 becomes activated, the first charge pump 312 may begin accumulating energy from the antenna 130 (e.g., driven by the input voltages $V_{LL}$ and $V_{RR}$) and generate a voltage that is a certain multiple (e.g., double) of the input voltages $V_{LL}$ and $V_{RR}$. The voltage generated by the first charge pump 312 may contribute to the gradual ramp up of the supply voltage $V_{DD\_STM}$ by providing an incremental amount of voltage. Meanwhile, when the first charge pump 312 reaches its maximum voltage, the second charge pump 314 may be activated to accumulate energy from the antenna 130. The operations of the second charge pump 314 may further contribute to the gradual ramp up of the supply voltage $V_{DD\_STM}$ by providing an additional increment of voltage that is a certain multiple (e.g., double) of the input voltages $V_{LL}$ and $V_{RR}$. According to some example embodiments, each voltage multiplier along the first current path 310 in the voltage supply generator 122 may contribute to the gradual ramp of the positive supply voltage $V_{DD\_STM}$ by providing a voltage increment that is a certain multiple (e.g., double) of the input voltages $V_{LL}$ and $V_{RR}$ (e.g., associated with the radio frequency energy from the antenna 130).

In some example embodiments, each voltage multiplier along the second current path 320 in the voltage supply generator 122 may contribute to the gradual ramp up of the negative supply voltage $V_{SS\_STM}$. For instance, the third charge pump 322 may generate a voltage that is a certain multiple (e.g., double) of the input voltages $V_{LL}$ and $V_{RR}$ (e.g., associated with the radio frequency energy from the antenna 130). The voltage generated by the third charge pump 322 provides an increment to the input voltages $V_{LL}$ and $V_{RR}$. Similarly, the fourth charge pump 324 may also provide an additional voltage increment that is a certain multiple (e.g., double) of the input voltages $V_{LL}$ and $V_{RR}$. The fourth charge pump 324 may be activated when the third charge pump 322 reaches its maximum voltage.

Figure 4:
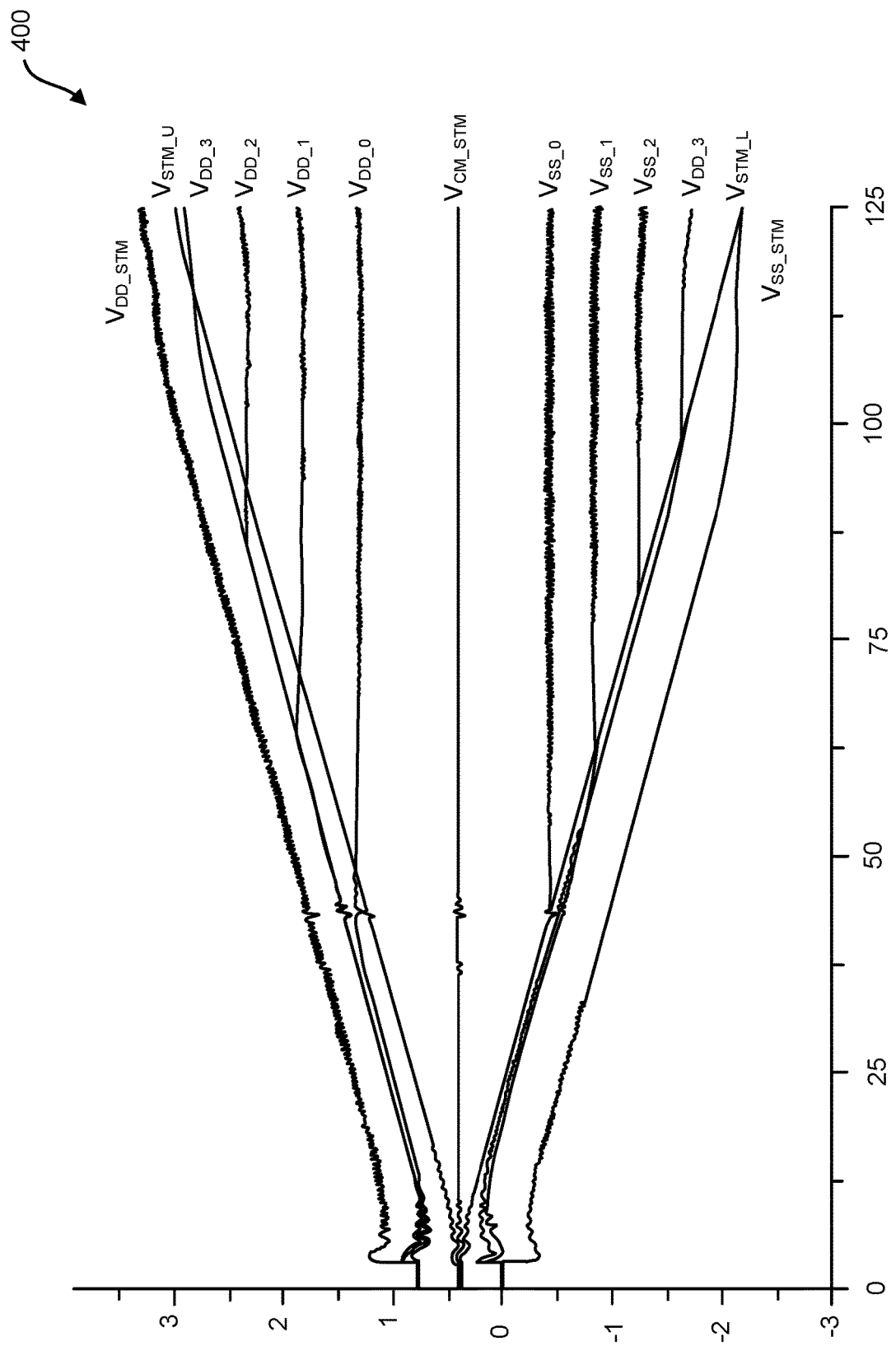
FIG. 4 depicts a graph illustrating a gradual ramp of a positive voltage supply and a negative voltage supply, in accordance with some example embodiments.

FIG. 4 depicts a graph illustrating a gradual ramp of a positive voltage supply $V_{DD\_STM}$ and a negative voltage supply $V_{SS\_STM}$, in accordance with some example embodiments. Referring to FIGS. 3-4, the internal voltages $V_{DD}$ and $V_{SS}$ of the charge multipliers in the voltage supply generator 124 may be initially low (e.g., at a common mode voltage $V_{CM\_STM}$). The internal voltages $V_{DD}$ and $V_{SS}$ of the charge multipliers subsequently increase in response to an increase in the voltages $V_{STM\_U}$ and $V_{STM\_L}$ at one or more electrodes in the electrode array 150. For example, the internal voltages $V_{DD\_0}$ and $V_{SS\_0}$ of the first charge pump 312 may increase in response to the increase in the voltages $V_{STM\_U}$ and $V_{STM\_L}$ at the electrodes. Similarly, the internal voltages $V_{DD\_1}$ and $V_{SS\_1}$ of the second charge pump 314 may also increase in response to the increase in the voltages $V_{STM\_U}$ and $V_{STM\_L}$ at the electrodes. The increase in the internal voltages $V_{DD}$ and $V_{SS}$ at each individual charge multiplier may contribute to a gradual ramp up of the positive voltage supply $V_{DD\_STM}$ and the negative voltage supply $V_{SS\_STM}$ provided by the voltage supply generator 124.

Figure 5A:
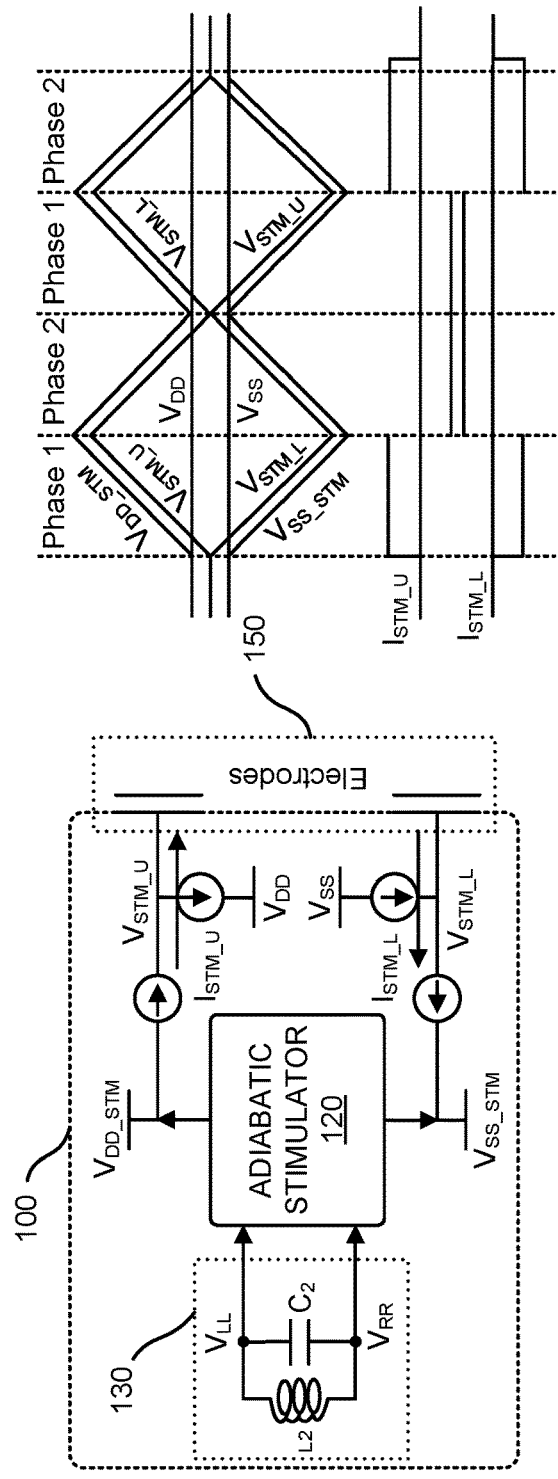
FIG. 5A depicts an operation of a neural stimulator during a first energy provision phase, in accordance with some example embodiments.

FIG. 5A depicts an operation of the neural stimulator 100 during a first energy provision phase, in accordance with some example embodiments. Referring to FIGS. 1-5A, the adiabatic stimulator 120 may be configured to generate the voltage supplies $V_{DD\_STM}$ and $V_{SS\_STM}$ at least by incrementally ramping up the voltages $V_{DD}$ and $V_{SS}$ of the radio frequency energy from the antenna 130. The voltage supplies $V_{DD\_STM}$ and $V_{SS\_STM}$ may drive a current through one or more electrodes in the electrode array 150. As shown in FIG. 5A, a current $I_{STM\_U}$ flows from the positive voltage supply $V_{DD\_STM}$ to the electrode array 150 while a return current $V_{STM\_L}$ flows from the electrode 150 back to the negative voltage supply $V_{SS\_STM}$. As such, during the energy provision phase, the voltages $V_{STM\_U}$ and $V_{STM\_L}$ at the electrode array 150 may track the voltages at the voltage supplies $V_{DD\_STM}$ and $V_{SS\_STM}$. Charge may be stored across one or more electrodes in the electrode array 150 during the first energy provision phase.

Figure 5B:
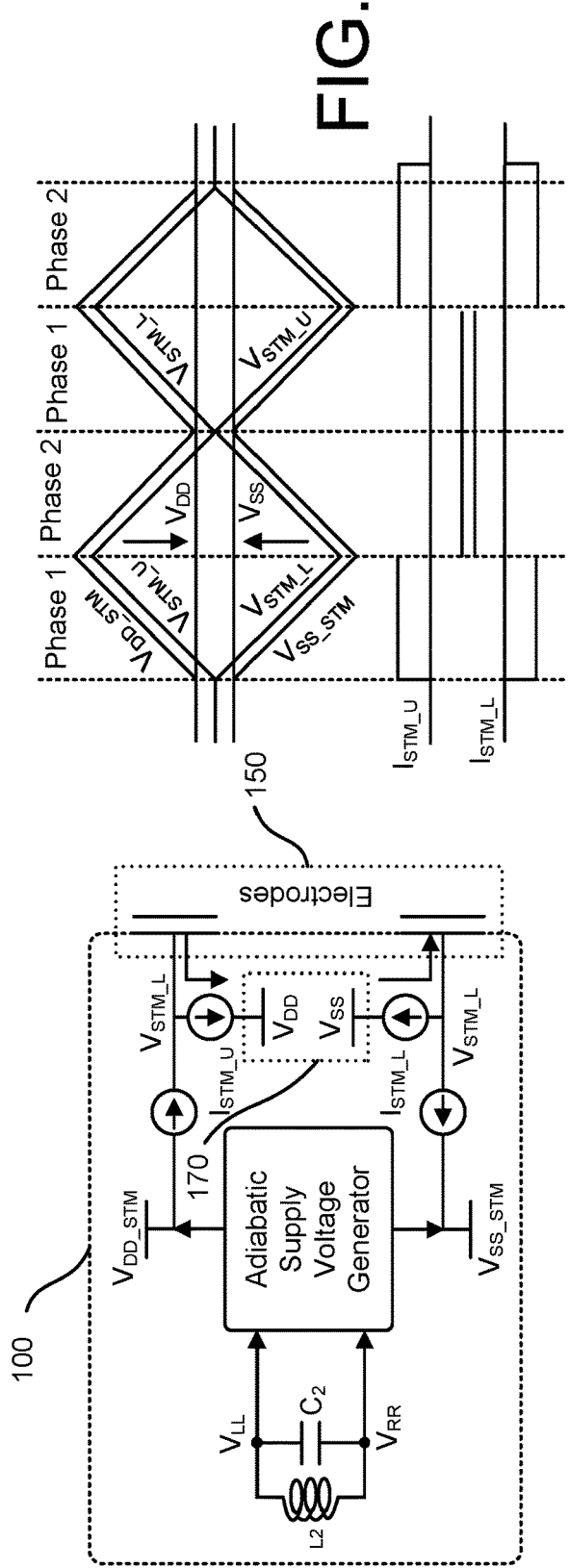
FIG. 5B depicts an operation of a neural stimulator during a first energy replenishment phase, in accordance with some example embodiments.

FIG. 5B depicts an operation of the neural stimulator 100 during a first energy replenishment phase, in accordance with some example embodiments. Referring to FIGS. 1-5B, charge stored across one or more electrodes in the electrode array 150 may be recycled during the first energy replenishment phase, which may follow the first energy provision phase described with respect to FIG. 5A. As shown in FIG. 5B, charge stored across one or more electrodes in the electrode array 150 may be returned via the currents the $I_{STM\_U}$ and $I_{STM\_L}$ to the voltage supplies $V_{DD}$ and $V_{SS}$ of the power source 170. The recycled energy stored at the power source 170 may be used to power one or more operations of the neural stimulator 100 including, for example, control, configuration, voltage bias generation, communication, and recording.

FIG. 5C depicts an operation of the neural stimulator 100 during a second energy provision phase, in accordance with some example embodiments. Referring to FIG. 1-5C, the adiabatic stimulator 120 may continue to generate the voltage supplies $V_{DD\_STM}$ and $V_{SS\_STM}$ subsequent to an energy replenishment phase (e.g., the first energy replenishment phase described with respect to FIG. 5B). For instance, during the second energy provision phase, the adiabatic stimulator may incrementally ramp up the voltages $V_{DD}$ and $V_{SS}$ of the radio frequency energy from the antenna 130 to generate the voltage supplies $V_{DD\_STM}$ and $V_{SS\_STM}$. According to some example embodiments, the adiabatic stimulator 120 may alternate the direction of the currents $I_{STM\_U}$ and $I_{STM\_L}$ between consecutive energy provision phases. As shown in FIG. 5C, the switch matrix 140 may change the electrode connections such that neural stimulation may continue but with an opposite polarity than during a previous energy provision phase (e.g., the first energy provision phase described with respect to FIG. 5A). During the second energy provision phase, the voltages $V_{STM\_U}$ and $V_{STM\_L}$ at the electrode array 150 may continue track the voltages at the voltage supplies $V_{DD\_STM}$ and $V_{SS\_STM}$ (e.g., as during the first energy provision phase described with respect to FIG. 5A).

FIG. 5D depicts an operation of the neural stimulator 100 during a second energy replenishment phase, in accordance with some example embodiments. Referring to FIGS. 1-5D, charge stored across one or more electrodes in the electrode array 150 may be recycled during the second energy replenishment phase, which may follow the second energy provision phase described with respect to FIG. 5B. As shown in FIG. 5D, charge stored across one or more electrodes in the electrode array 150 may be returned via the currents the $I_{STM\_U}$ and $I_{STM\_L}$ to the voltage supplies $V_{DD}$ and $V_{SS}$ of the power source 170. The recycled energy stored at the power source 170 may be used to power one or more operations of the neural stimulator 100 including, for example, control, configuration, voltage bias generation, communication, and recording.

Figure 5E:
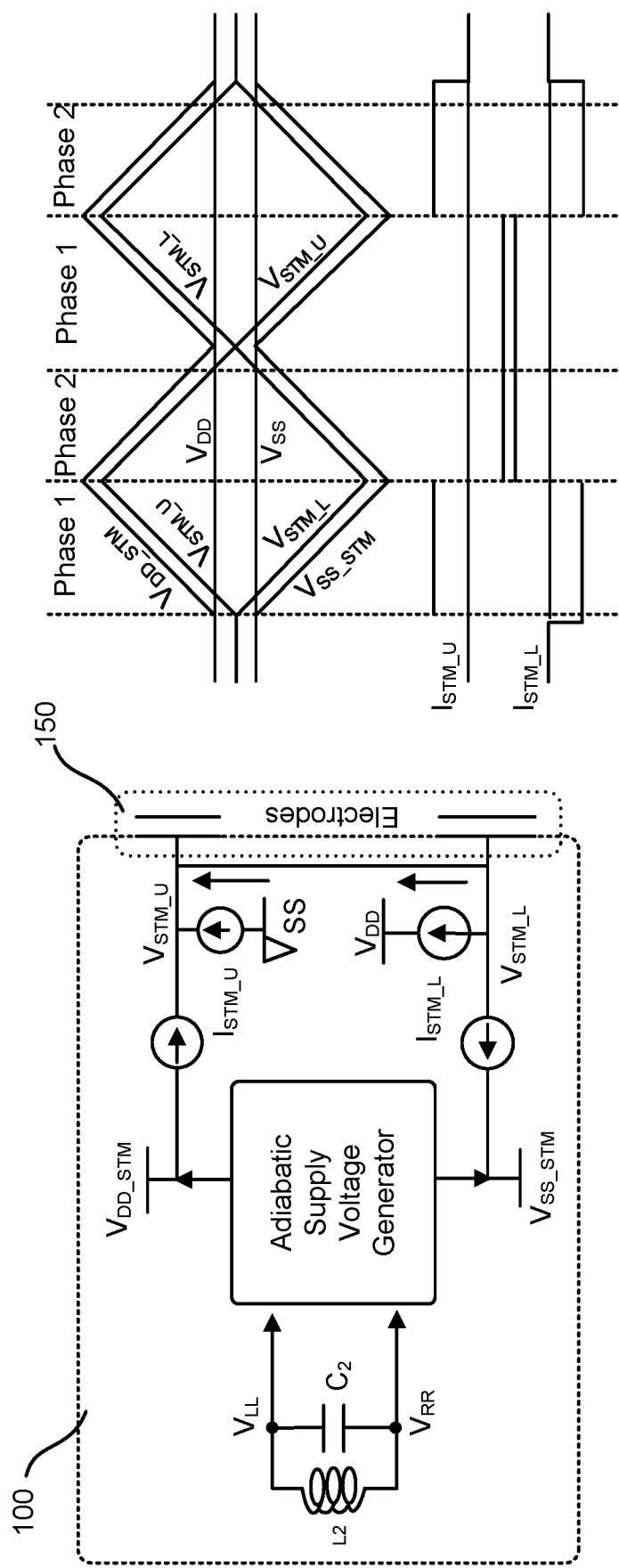
FIG. 5E depicts an operation of a neural stimulator during a termination phase, in accordance with some example embodiments.

FIG. 5E depicts an operation of the neural stimulator 100 during a termination phase, in accordance with some example embodiments. Referring to FIGS. 1-5E, any residual charge that is not recycled during a previous energy replenishment phase (e.g., the second energy replenishment phase described with respect to FIG. 5D) may be released. For instance, as shown in FIG. 5E, the residual charges may be released by creating a short circuit across one or more electrodes in the electrode array 150.

Figure 6:
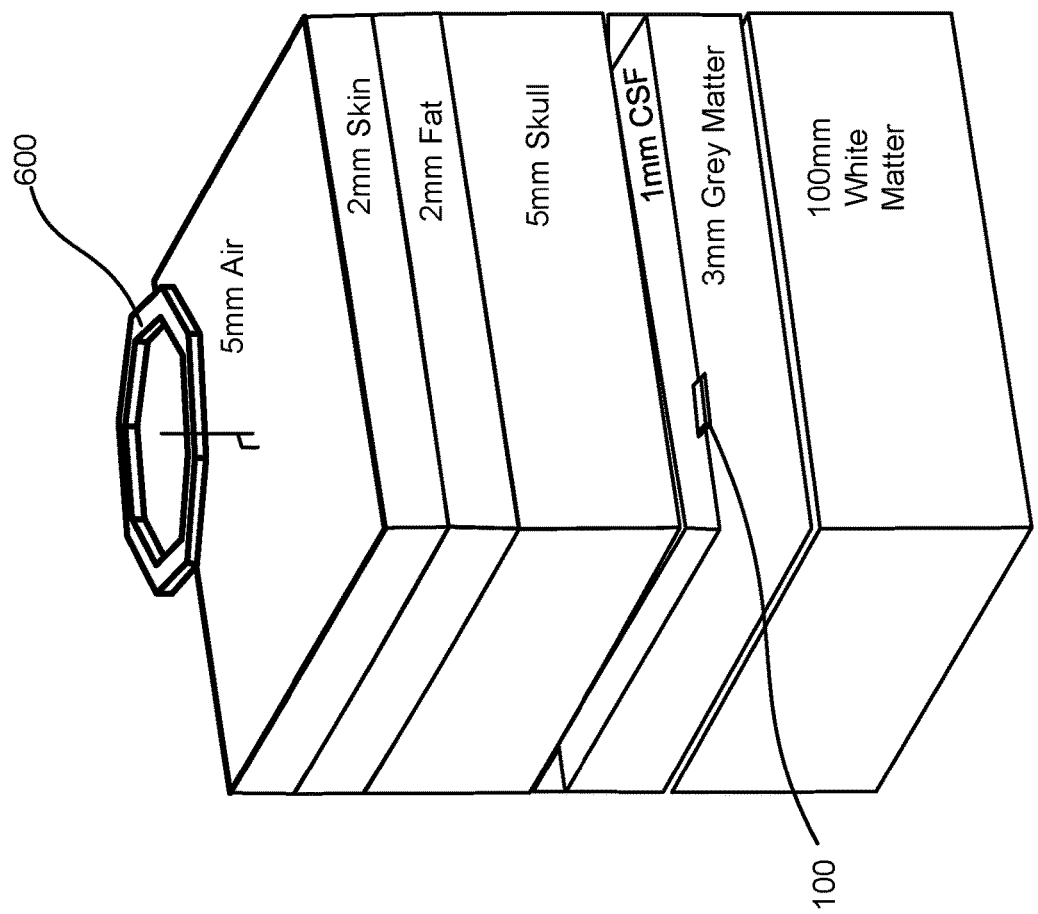
FIG. 6 depicts an placement of a neural stimulator, in accordance with some example embodiments.

FIG. 6 depicts a placement of the neural stimulator 100, in accordance with some example embodiments. Referring to FIGS. 1 and 6, the neural stimulator 100 may be implanted along the grey matter of the brain beneath the scalp, skull, and layer of cerebrospinal fluid (CSF). As shown in FIG. 6, the neural stimulator 100 may be powered by an external transmitter 600. For instance, the transmitter 600 may be adapted to provide radio frequency energy to the neural stimulator 100. In addition, the transmitter 600 may be further configured to configure the neural stimulator 100 by wireless transmitting one or more instructions to the neural stimulator 100.

Figure 7:
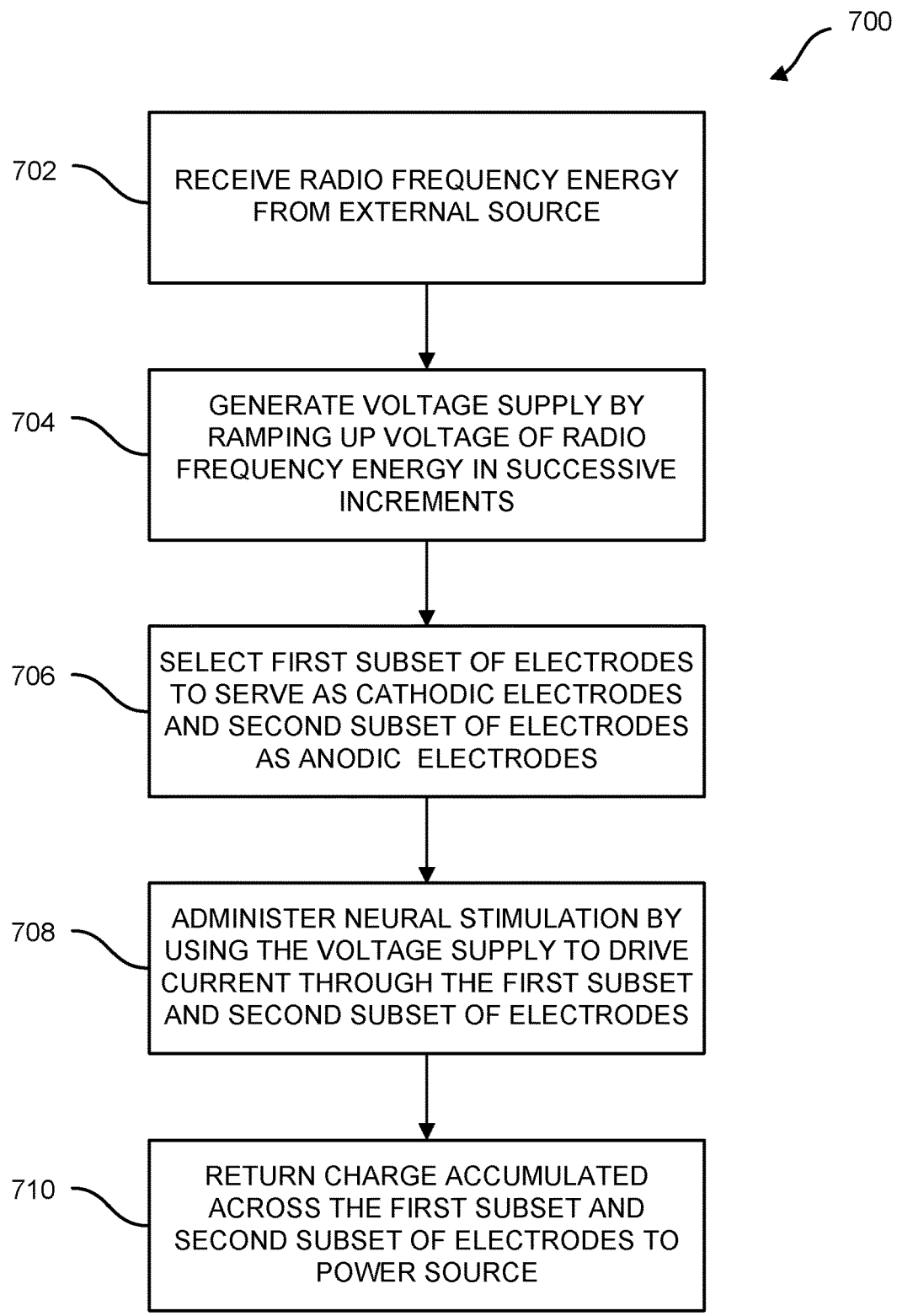
FIG. 7 depicts a flowchart illustrating a process for analog-to-digital conversion, in accordance with some example embodiments.

FIG. 7 depicts a flowchart illustrating a process 700 for administering neural stimulation, in accordance with some example embodiments. Referring to FIGS. 1-7, the process 700 may be performed by the neural stimulator 100.

At 702, the neural stimulator 100 (e.g., the antenna 130) may receive radio frequency energy. For instance, the neural stimulator 100 (e.g., the antenna 130) may receive radio frequency energy from an external source (e.g., the transmitter 600).

At 704, the neural stimulator 100 (e.g., the adiabatic stimulator 120) may generate a voltage supply at least by ramping up a voltage of the radio frequency energy in successive increments. For example, the adiabatic stimulator 120 may include the voltage supply generator 124, which may include a plurality of charge multipliers (e.g., the first charge pump 312, the second charge pump 314). The charge multipliers may be activated in succession (e.g., one after another) to generate, at each charge multiplier, a voltage that is a multiple (e.g., double) of the voltage of the radio frequency energy. For example, the first charge pump 312 may be activated to generate a voltage while the second charge pump 314 may be activated to generate an additional voltage when the first charge pump 312 reaches its maximum voltage. As such, the charge multipliers may be activated one after another to successively increment the voltage of the radio frequency energy in order to provide a voltage supply that is sufficiently high for neural stimulation (e.g., 8-9 volts).

At 706, the neural stimulator 100 (e.g., the control unit 100) may select a first subset of electrodes to serve as cathodic electrodes and a second subset of electrodes to serve as anodic electrodes. For example, the control unit 100 may select one or more electrodes in the electrode array 150 in accordance with a particular treatment site. The treatment site where the neural stimulator 100 applies electric stimulation may be preconfigured and/or determined based on subsequent configurations (e.g., instructions from the transmitter 600).

According to some example embodiments, the control unit 100 may select the first subset of electrodes (e.g., the first electrode 152) to act as the cathodic electrodes and a second subset of electrodes (e.g., the second electrode 154) to act as the anodic electrodes such that current driven through the electrode array 150 may travel from the cathodic electrodes to the anodic electrodes. In some example embodiments, the control unit 100 may select the first and second subset of electrodes at least by controlling the operations of the switch matrix 140. The switch matrix 140 may change the routing between adiabatic stimulator 120 (e.g., the voltage supply generator 122) and one or more electrodes in the electrode array 150 in order to direct the flow of current to and from the first and second subset of electrodes.

At 708, the neural stimulator 100 may administer neural stimulation at least by using the voltage supply to drive a current through the first subset of electrodes and the second subset of electrodes. In some example embodiments, the neural stimulator 100 may administer neural stimulation during the energy provision phase. During the energy provision phase, the voltage supply generated by the adiabatic stimulator 120 (e.g., the voltage supply generator 122) may drive a current through the select electrodes in the electrode array 150 (e.g., from the first subset of electrodes to the second subset of electrodes).

At 710, the neural stimulator 100 may return charge accumulated across the first subset of electrodes and the second subset of electrodes to the power source 170. In some example embodiments, the energy used for neural stimulation during an energy provision phase (e.g., in operation 708) may be recycled during a subsequent energy replenishment phase. For instance, the neural stimulator 100 may return the charge that has accumulated at one or more electrodes in the electrode array 150 to the power source 170. The recycled energy stored at the power source 170 may be used to power one or more other operations of the neural stimulator 100 including, for example, control, configuration, voltage bias generation, communication, and recording (e.g., of intracranial electroencephalography).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. An apparatus for neural stimulation, comprising:
    an antenna configured to receive, from an external source, radio frequency energy;
    a plurality of electrodes;
    a voltage supply generator configured to generate a voltage supply by at least ramping up a voltage of the radio frequency energy in successive increments, wherein the voltage supply drives a current to the plurality of electrodes during the neural stimulation;
    a current controller configured to at least route the current to the plurality of electrodes during an energy provision phase of neural stimulation, and route the current from the plurality of electrodes to a power source during an energy replenishment phase of neural stimulation; and
    a control unit configured to at least cause the current controller to change the routing of the current between the energy provision phase and the energy replenishment phase.

2. The apparatus of claim 1, wherein the current controller is further configured to create a short circuit between the plurality of electrodes during a termination phase of neural stimulation, and wherein creating the short circuit releases energy that is not returned to the power source during a previous energy replenishment phase of neural stimulation.

3. The apparatus of claim 1, wherein the power source is configured to provide energy for one or more of a control, a configuration, a voltage bias generation, a communication, and a recording by the apparatus.

4. The apparatus of claim 1, further comprising a control unit configured to at least:
    cause the current controller to change the routing of the current between successive phases of the energy provision phase and the energy replenishment phase;
    select, based at least in part on a location of the neural stimulation, a first subset of electrodes and a second subset of electrodes from the plurality of electrodes; and
    designate the first subset of electrodes to serve as cathodic electrodes and the second subset of electrodes to serve as anodic electrodes.

5. The apparatus of claim 4, further comprising a switch matrix configured direct, based at least in part on the selection and designation by the control unit, the current to flow from the cathodic electrodes to the anodic electrodes.

6. The apparatus of claim 4, wherein a third subset of electrodes is not selected, and wherein the third subset of electrodes remains inactive during neural stimulation.

7. The apparatus of claim 1, further comprising a communication unit configured to receive, from the external source, one or more instructions for configuring a stimulation waveform and/or a stimulation location.

8. The apparatus of claim 1, wherein the plurality of electrodes comprises capacitive electrodes and/or pseudo capacitive electrodes.

9. The apparatus of claim 1, wherein the voltage supply generator comprises a first voltage multiplier and a second voltage multiplier, wherein the first voltage multiplier is configured to generate a first voltage that comprises a first increment to the voltage of the radio frequency energy, wherein the second voltage multiplier is configured to generate a second voltage that comprises a second increment to the voltage of the radio frequency energy, wherein the second voltage multiplier generates the second voltage when the first voltage multiplier reaches a maximum voltage, and wherein the first voltage multiplier and/or the second voltage multiplier comprises a charge pump.

10. A method for neural stimulation, comprising:
    receiving, using an antenna, radio frequency energy, wherein the radio frequency energy is received from an external source;
    generating, at a voltage supply generator, a voltage supply by at least ramping up a voltage of the radio frequency energy in successive increments, wherein the voltage supply drives a current to a plurality of electrodes during the neural stimulation;
    routing, by a current controller, the current to the plurality of electrodes during an energy provision phase of neural stimulation;
    routing, by the current controller, the current from the plurality of electrodes to a power source during an energy replenishment phase of neural stimulation; and
    causing, by a control unit, a change in the routing of the current between the energy provision phase and the energy replenishment phase.

11. The method of claim 10, further comprising creating, by the current controller, a short circuit between the plurality of electrodes during a termination phase of neural stimulation, wherein creating the short circuit releases energy that is not returned to the power source during a previous energy replenishment phase of neural stimulation.

12. The method of claim 10, further comprising providing, by the power source, energy for the performance of one or more of a control, a configuration, a voltage bias generation, a communication, and a recording.

13. The method of claim 10, further comprising:
causing, by a control unit, a change in the routing of the current between successive phases of the energy provision phase and the energy replenishment phase;
selecting, by the control unit, a first subset of electrodes and a second subset of electrodes from the plurality of electrodes, the selecting based at least in part on a location of the neural stimulation;
designating, by the control unit, the first subset of electrodes to serve as cathodic electrodes and the second subset of electrodes to serve as anodic electrodes; and
directing, by a switch matrix, the current to flow from the cathodic electrodes to the anodic electrodes, wherein the directing is based at least in part on the selection and designation by the control unit.

14. The method of claim 13, wherein a third subset of electrodes is not selected, and wherein the third subset of electrodes remains inactive during neural stimulation.

15. The method of claim 10, further comprising receiving, at a communication unit, one or more instructions for configuring a stimulation waveform and/or a stimulation location, wherein the one or more instructions are received from the external source.

16. The method of claim 10, further comprising:
generating, by a first voltage multiplier, a first voltage that comprises a first increment to the voltage of the radio frequency energy; and
generating, by a second voltage multiplier, a second voltage that comprises a second increment to the voltage of the radio frequency energy.

17. The method of claim 16, wherein the second voltage multiplier generates the second voltage when the first voltage multiplier reaches a maximum voltage.

18. A non-transitory computer-readable storage medium including program code which when executed by at least one processor causes operations comprising:
receiving, using an antenna, radio frequency energy, wherein the radio frequency energy is received from an external source;
generating, at a voltage supply generator, a voltage supply by at least ramping up a voltage of the radio frequency energy in successive increments, wherein the voltage supply drives a current to a plurality of electrodes during the neural stimulation;
routing, by a current controller, the current to the plurality of electrodes during an energy provision phase of neural stimulation;
routing, by the current controller, the current from the plurality of electrodes to a power source during an energy replenishment phase of neural stimulation; and
causing, by a control unit, a change in the routing of the current between the energy provision phase and the energy replenishment phase.

* * * * *